US006425924B1

(12) United States Patent
Rousseau (10) Patent No.: US 6,425,924 B1
(45) Date of Patent: Jul. 30, 2002

(54) HERNIA REPAIR PROSTHESIS (75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/540,793

(22) Filed: Mar. 31, 2000

(51) Int. Cl.[7] .................................................. A61F 2/02
(52) U.S. Cl. ..................................... 623/23.64; 606/151
(58) Field of Search ........................... 623/23.64, 23.65, 623/23.7–23.72, 23.75; 606/151, 213

(56) References Cited

U.S. PATENT DOCUMENTS

| | | | |
|---|---|---|---|
| 4,744,364 A | 5/1988 | Kensey | |
| 4,852,568 A | 8/1989 | Kensey | |
| 5,021,059 A | 6/1991 | Kensey et al. | |
| 5,061,274 A | 10/1991 | Kensey | |
| 5,108,420 A | 4/1992 | Marks | |
| 5,116,357 A | 5/1992 | Eberbach | |
| 5,192,302 A | 3/1993 | Kensey et al. | |
| 5,254,133 A | 10/1993 | Seid | |
| 5,356,432 A | * 10/1994 | Rutkow et al. | 623/23.72 |
| 5,379,754 A | * 1/1995 | Tovey et al. | 128/4 |
| 5,397,331 A | 3/1995 | Himpens et al. | |
| 5,456,720 A | 10/1995 | Schultz et al. | |
| 5,545,178 A | 8/1996 | Kensey et al. | |
| 5,634,931 A | 6/1997 | Kugel | |
| 5,686,090 A | * 11/1997 | Schilder et al. | 424/423 |
| 5,716,408 A | 2/1998 | Eldridge et al. | |
| 5,769,864 A | 6/1998 | Kugel | |
| 5,861,036 A | * 1/1999 | Godin | 623/23.65 |
| 5,916,225 A | 6/1999 | Kugel | |
| 5,944,738 A | 8/1999 | Amplatz et al. | |
| D416,327 S | 11/1999 | Kugel | |
| 5,976,174 A | * 11/1999 | Ruiz | 606/213 |
| 6,066,777 A | * 5/2000 | Benchetrit | 623/11.11 |
| 6,113,641 A | * 9/2000 | Leroy et al. | 623/23.75 |
| 6,166,286 A | * 12/2000 | Trabucco | 623/11.11 |
| 6,180,848 B1 | * 1/2001 | Flament et al. | 623/11.11 |

\* cited by examiner

Primary Examiner—David H. Willse
Assistant Examiner—Suzette J. Jackson

(57) ABSTRACT

The present invention is directed to prostheses containing a radially-expandable member for placement within and occlusion of a hernia opening, which member is made from a biocompatible, flexible, porous textile suitable for reinforcing tissue.

14 Claims, 11 Drawing Sheets

HERNIA REPAIR PROSTHESIS

FIELD OF THE INVENTION

The present invention relates to an implantable hernia repair prosthesis and a method for reinforcing and repairing damaged tissue or muscle walls.

BACKGROUND OF THE INVENTION

Various prosthetic mesh materials have been proposed to reinforce the abdominal wall and to close abdominal wall defects utilizing different repair prostheses and methods of installation. The methods of executing a surgical repair can be segregated into two main approaches. The repair can be made exclusively from the anterior side (closest to the surgeon) of the defect by dissecting the sac free of the fascia and pressing it back into the pre-peritoneal space and providing permanent closure of the defect. The closure can be provided through the application of space filling prostheses and overlay patches (tension-free techniques) or can be accomplished through the use of sutures (tension techniques).

An example of a tension free anterior repair is to fold a sheet of surgical mesh fabric into a multi-layer cone configuration and then to insert the mesh plug into a hernia defect to occlude the void. Such a multi-layer prosthesis is inherently stiff and may not fully conform to variations in the contour of the defect, leaving gaps between the implant and the abdominal wall that potentially could lead to recurrent herniation. The stiff, multi-layered mesh plug also may be susceptible to kinking and buckling during placement.

U.S. Pat. No. 5,356,432, discloses an implantable prosthesis that is a conical plug formed of a knitted polypropylene monofilament mesh fabric. Longitudinal pleats are hot molded into the mesh body to enhance the flexibility of the conical implant, ideally allowing the implant to closely match the contour of the herniated opening when compressed within the defect. When the device is installed into a fascial defect, the tip of the conical shaped plug presses into and against the visceral sac, potentially enabling long-term erosion of the peritoneum and underlying viscera. The device, in one embodiment, has filler material incorporated into the interior of the formed mesh cone in an attempt to minimize contraction of the device during healing. As collagen scar tissue grows into the prosthetic material, the cross linking of the maturing collagen fibers causes the scar tissue (and encapsulated plug device) to contract. This contraction of scar tissue within the defect and plug causes the surrounding diseased tissue to be subjected to tension, thus enabling re-occurrence of the hernia along the edge of the conical plug. The use of the device requires the passage of a pre-expanded plug through the hernia defect and relies upon the radial expansion force of the single layer mesh cone and filler leaves to occlude the defect. Additionally, since the plug is secured in position by anchoring to the surrounding diseased tissue, the device may dislodge and migrate within the pre-peritoneal space.

Alternatively, a defect may be repaired through the use of posterior approaches that provide various prosthetic devices in the pre-peritoneal space to prevent the peritoneum from entering the fascial defect. These devices, in some cases, require the use of laparoscopic techniques and, in other cases, require the application of the prosthesis from a remote location under the defect to be repaired. Examples of posterior approaches are disclosed in U.S. Pat. Nos. 5,116,357, 5,254,133 and 5,916,225. However, in many cases, procedures utilizing such devices are complicated, in addition to requiring the use of general anesthesia and costly disposable instrumentation to support the laparoscopic surgery.

Accordingly, the prior art lacks an implantable hernia repair prosthesis for occluding and repairing damaged muscle and tissue wall ruptures, that is adaptable to irregularities in the shape of the defect, is simple to install, does not require the use of general anesthesia during installation and resists radial collapse due to tissue incorporation.

SUMMARY OF THE INVENTION

The present invention is directed to prostheses comprising a radially-expandable member for placement within and occlusion of a hernia opening. The expandable member comprises a biocompatible, flexible, porous textile suitable for reinforcing tissue. The invention also is directed to methods of reinforcing tissue and occluding tissue defects.

DETAILED DESCRIPTION OF THE INVENTION

The present invention provides implantable prostheses and methods for reinforcing and repairing weakened abdominal walls. The prostheses are formed of a biologically compatible, flexible and porous medical textile suitable for reinforcing tissue and occluding tissue defects. The implantable prostheses are indicated particularly for the repair of hernias in the abdominal cavity, including inguinal (direct and indirect), femoral, incisional and recurrent, and provide at least a partial posterior repair. The prostheses are able to be inserted easily in a stress-free condition into a fascia defect from an anterior approach and are capable of expanding radially, at least partially into the pre-peritoneal space, to substantially occlude and conform to the fascia wall of a fascia defect. The prostheses are suitable for the repair of varying sizes and shapes of hernias and can be anchored to the surrounding healthy tissue to prevent migration, thus extending beyond the edge of the defect on the anterior side of the defect. Other features of the present invention will become apparent from the following detailed description when taken in connection with the accompanying drawings that disclose multiple embodiments of the invention. The drawings are for the purpose of illustration only and are not intended as a definition of the limits of the invention.

The prostheses of the present invention comprise a hollow, radially-expandable member for placement within and occlusion of a fascia defect. By radially-expandable, it is meant that the cross sectional area of the member expands from an initial, non-expanded configuration having an initial cross sectional area, sized such that the member may be placed within a fascia defect in a stress-free condition, to a final, expanded configuration having a final cross sectional area greater than the initial cross sectional area and effective to occlude all of, or at least a substantial portion of, the fascia defect. This member can be manufactured out of biocompatible absorbable or non-absorbable material.

The prosthesis also comprises means for securing the prosthesis to the tissue wall. In certain embodiments, the means for securing comprises an overlay sheet of medical textile fixedly or maneuverably attached to the radially-expandable member, as depicted in the figures. When maneuverably, e.g. slideably, attached to the expandable member, the overlay sheet may be so-attached to the radially-expandable memberby the use of a filament, or multiple filaments, passed through the looped suture or the proximal end of the expandable member and attached to the overlay patch at the terminal ends of the filament. Prostheses comprising such a slideably, or maneuverably, attached means for securing the prostheses to the tissue wall and a member for occluding the defect also are included within the scope of inventions disclosed herein. In such embodiments, the occluding member need not be radially-expandable, but need only be effective to occlude the defect. One of the advantages of such a prosthesis is that, once placed into the defect area, the securing means may be maneuvered such that attachment to stable or healthy tissue may be accomplished, thereby providing a more secure attachment to the tissue wall.

In other embodiments, the means for securing the prosthesis may be an integral part of the radially-expandable member. The prosthesis is passed into/through a defect in the fascial layer. The radially-expandable member then is collapsed axially, thus causing radial expansion of the radially-expandable member. The radial expansion of the radially-expandable member causes substantially complete occlusion of the fascial defect.

Slideable, or otherwise maneuverable, attachment of the radially-expandable member to the means for securing permits the overlay member to be maneuvered relative to the deployed expandable member and adjusted once placed within the fascia defect. This provides added benefit of being positionable, relative to the cord and other anatomical structures once in place, over conventional prostheses for repairing fascia defects which are fixedly attached to the means for securing to surrounding tissue, and are not capable of being adjusted once the prostheses are placed and fixed within the fascia defect.

While, radial expansion of the member may be effected by means for radially-expanding the member as discussed and depicted herein, prostheses that are self-expanding, i.e. self-collapsing, when placed in position within the fascia defect are included within the scope of the present invention. Such devices may be constructed such that they will deploy, i.e. collapse axially and radially-expand to occlude the defect, when positioned within a defect in response to conditions of the body surrounding the defect. Preferably, a looped suture, passed longitudinally through the hollow cavity of the radially-expandable member along the axis thereof, may serve as a means for radially-expanding the member.

In certain embodiments of the invention, the radially-expandable member comprises opposing conical members fixedly attached one to the other at their respective bases, thus forming a cavity defined by the attached conical members. Each cone comprises pleated surfaces that increase the axial rigidity of the prosthesis, thus allowing the prosthesis to exert a radial expansion force, while ultimately maintaining the ability to conform to irregularities in the tissue or muscle wall surrounding the opening. One or more tubular structure of textile material may be contained within the cavity of the radially-expandable member to impart additional axial rigidity to the prosthesis, thus improving the handling characteristics during insertion into the defect. Tubular structure, as used herein, is meant to include those structures where the cross sectional configuration is tubular in nature. Tubular structure specifically includes cylindrical rolls of materials, e.g. meshes, where the cross section configuration is circular, as well as structures where the cross sectional configuration may be elliptical, triangular, rectangular, etc. The tubular structure also improves the radial expandability of the prosthesis when it is compressed axially and the cylinder collapses, ensuring a solid expansion of the prosthesis against and below the tissue or wall structure defining the defect.

The prostheses and radially-expandable member may be constructed from any biologically compatible, flexible and porous medical textile suitable known for reinforcing tissue and occluding tissue defects. Preferred mesh materials include knitted polypropylene monofilament mesh fabrics such as those available from Ethicon, Inc. under the Prolene trademark, as well as meshes available from Ethicon, Inc. under the Vicryl trademark. Other mesh materials useful in the invention include those available under the Marlex, Dacron, Teflon and Merselene trademarks. Alternatively, the desired effect of forcing tissue re-generation under the overlay patch can be accomplished through the selection of biocompatible absorbable materials for use in the fabrication of the expandable member. Examples of suitable materials are Vicryl and Panacryl sutures, available from Ethicon, Inc, andpolysorb suture, available from United States Surgical Corporation.

Figure 1:
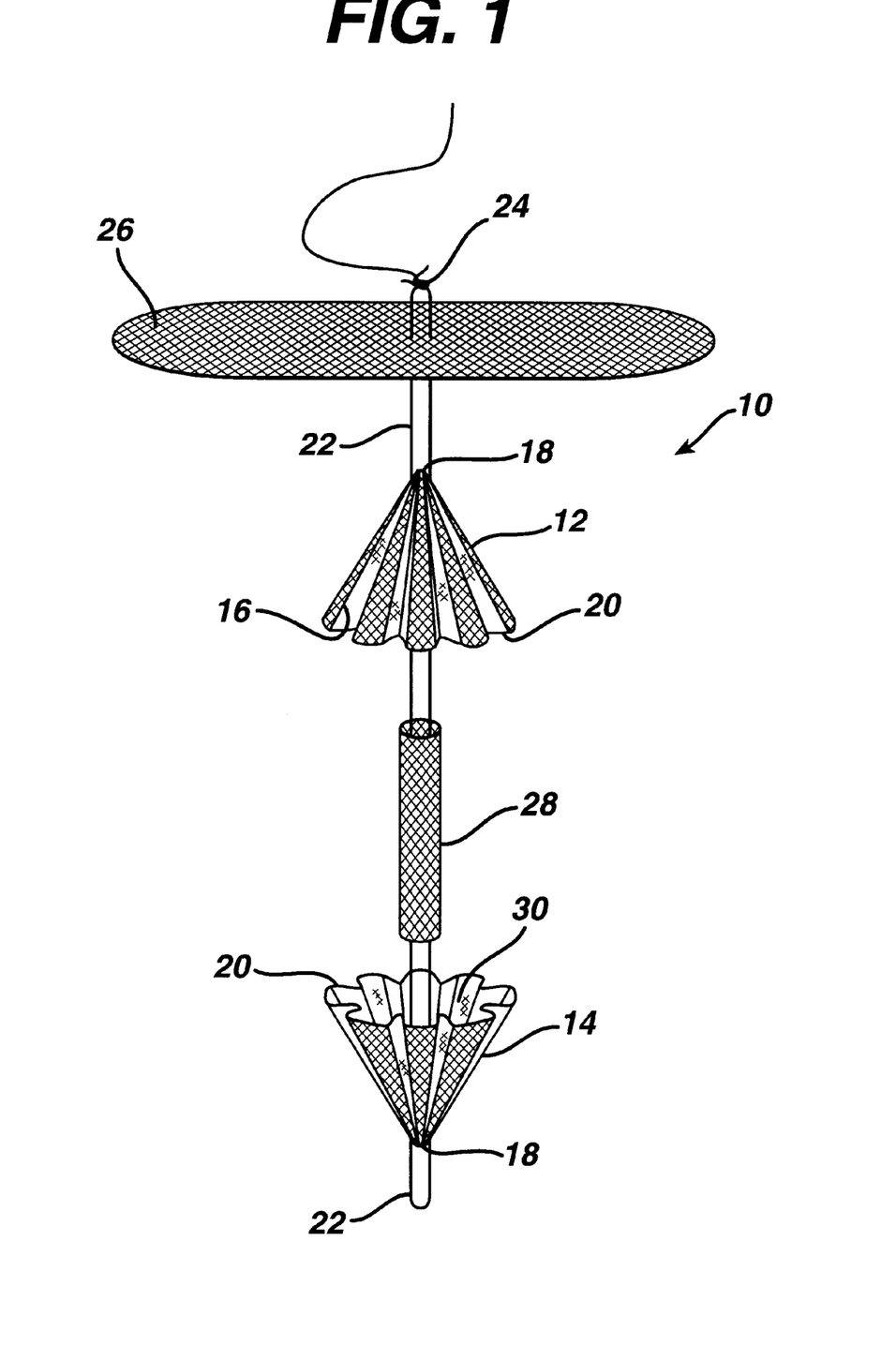
FIG. 1 is a perspective view of a prosthesis according to the present invention prior to assembly of all of its component parts.

An exploded view of a prosthesis of the present invention is illustrated in FIG. 1. Prosthesis 10 comprises radially-expandable member 12, comprising first and second conical members 14. Each conical member 14 comprises longitudinal pleats 16 terminating at apex 18 and base 20 of each cone, respectively. The number and spacial relationship of longitudinal pleats 16 are effective to enhance the axial rigidity of the prosthesis and to allow the prosthesis to more closely match the contour of the fascia defect when compressed and placed within the defect. Preferably, the pleats are thermoformed into the mesh body. Looped suture 22, with a non-reversing knot 24, is passed through the inner diameter of opposing conical members 14. Sheet 26 of polypropylene mesh is fixedly attached to apex 18 of one of opposing conical members 14 through the use of looped suture 22. Sheet 26 is utilized to attach and secure the prosthesis to the surrounding healthy tissue. optionally, prosthesis 10 may comprise one or more tubular structures, 28 of polypropylene mesh contained within cavity 30 formed when opposing conical members 14 are attached at their respective bases 20. Tubular structure 28 provides additional axial rigidity to the prosthesis during handling and insertion of the device into the defect.

Suture 22 is passed through the inner diameter of opposing cones 14, passing from the apex of one cone, through the apex of the second. Suture 22 then is looped and returned back through the inner diameter of the prosthesis in the opposite direction. Looped suture 22 is passed through the ends of tube 28 and causes tubular structure 28 to buckle, or collapse, when looped suture 22 is constricted during use. In the particular embodiment illustrated, both ends of looped suture 22 are passed through flat overlay sheet 26. Non-reversing knot 24 is tied in looped suture 22 and flat overlay sheet 26 is held in proximity to apex 18 of upper cone 14. The dead tail of the knot is trimmed to length. The finished prosthesis is subjected to sterilization prior to use.

Figure 2:
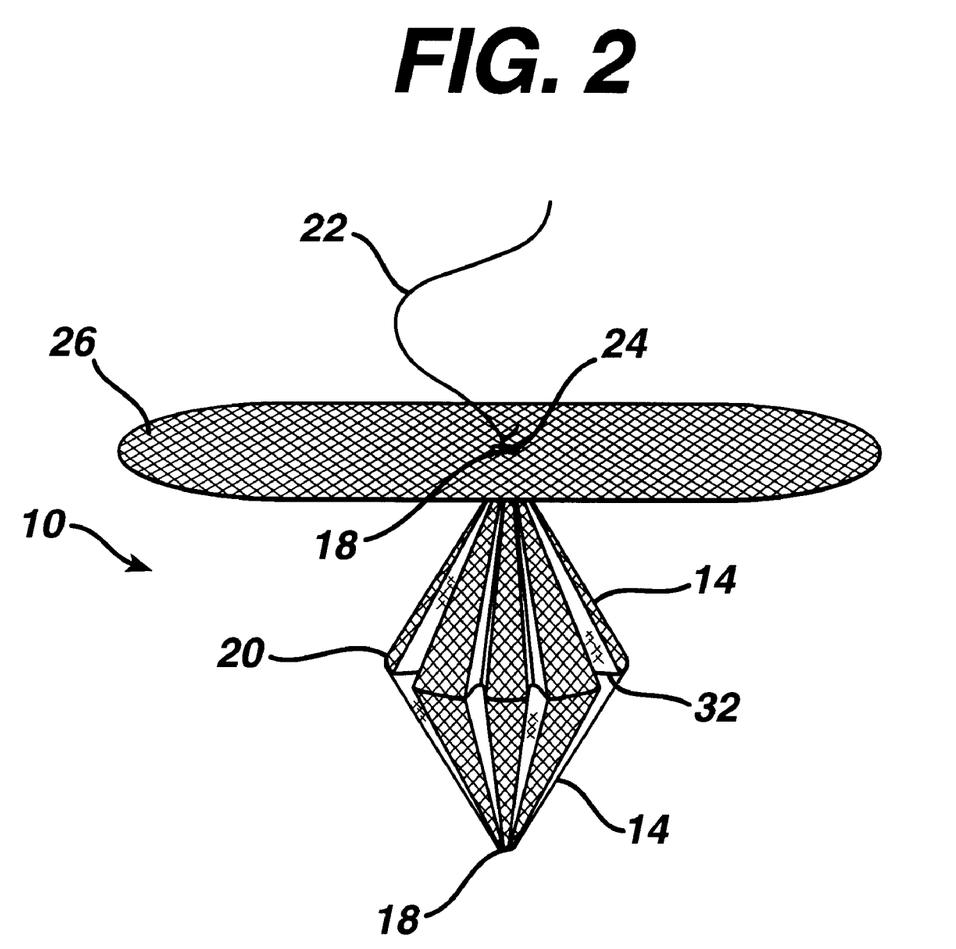
FIG. 2 is a perspective view of the assembled prosthesis depicted in FIG. 1.

The assembled prosthesis of FIG. 1 is illustrated in FIG. 2. Prosthesis 10 may be fabricated from any biocompatible medical woven, knitted or non-woven textile. In preferred embodiments, the prosthesis is fabricated from medical grade polypropylene mesh. Radially-expandable member 12 comprises conical members 14 fixedly attached one to the other at respective bases 20. Cones 14 are configured to have an initial, non-expanded, maximum diameter that is substantially the same size or less than the diameter of the defect to be repaired. While cones 14 are shown in the figure to be identical in structure, embodiments whereby one cone is taller than the second is contemplated by the invention. Cones 14 are positioned in opposition one to the other and bases 20 are aligned. Once bases 20 are aligned, cones 14 are fixedly attached to each other at respective bases 20. Bonding of cones 14 may be accomplished by stitching, welding or any other known form of fixable attachment, thus forming bond 32 about base 20. Preferably, prosthesis 10 comprises at least one flat sheet of mesh rolled into tubular structure 28 (FIG. 1) and permanently located within cavity 30 (FIG. 1) formed by fixedly attached cones 14. Tubular structure 28 is fabricated from a flat sheet of polypropylene mesh that, once rolled into cylindrical shape, can been secured about its circumference with suture. Alternatively, tubular structure 28 may be formed by rolling a flat sheet of mesh into the cylindrical configuration and welding, stitching or otherwise bonding the rolled sheet at the ends. Tubular structure 28 (FIG. 1) is disposed inside cavity 30 (FIG. 1) formed by fixedly attached opposing cones 14 and extends axially from internal apex 18 to internal apex 18 of cones 14. Cylinder 28 aids in providing axial rigidity to the prosthesis when it is inserted into the defect.

Figure 3:
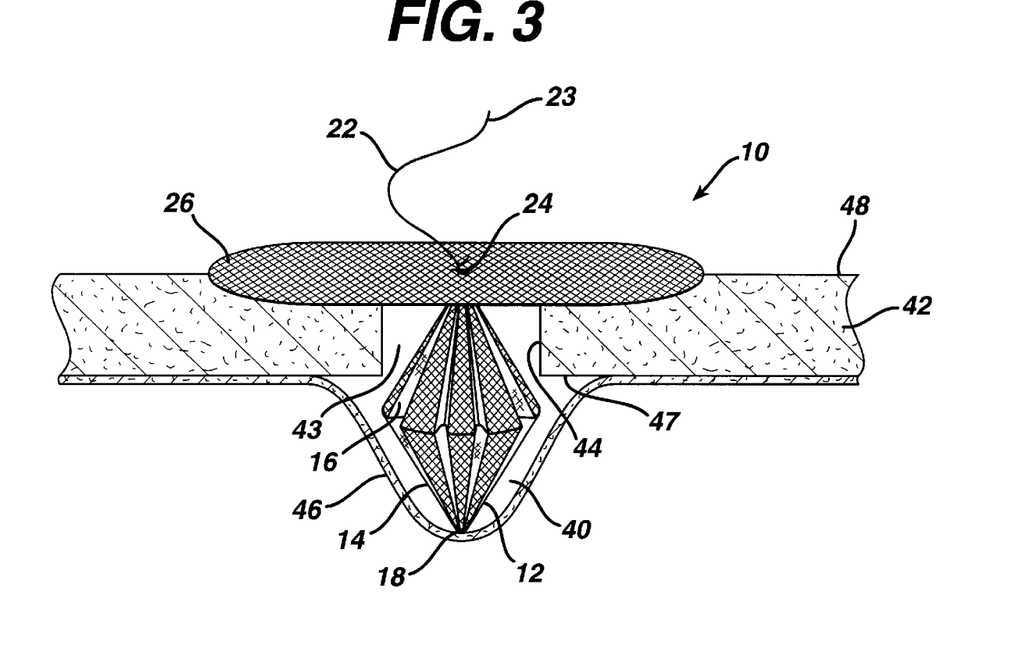
FIG. 3 is a perspective view of the prosthesis depicted in FIG. 2 when positioned within a defect in the fascia.
Figure 4:
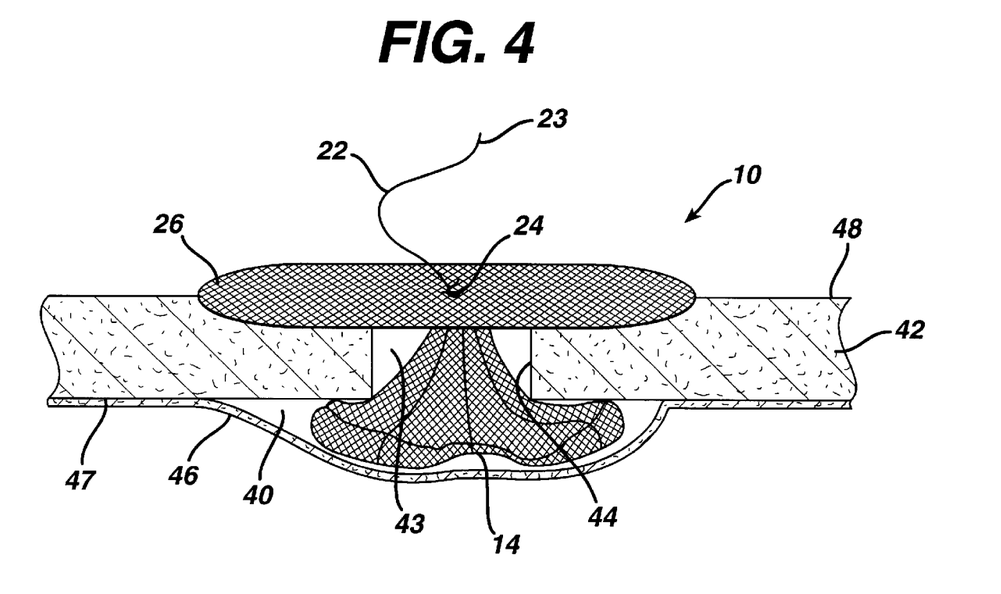
FIG. 4 is a prospective view of the prosthesis depicted in FIG. 3 after deployment, i.e. radial expansion, within the defect.

As shown in FIGS. 3 and 4, after hernia sac 40 has been dissected and/or ligated, prosthesis 10 is inserted into fascia defect 43. Once hernia sac 40 is free from walls 44 of defect 43 in fascia 42, hernia sac 40 is pressed back into the abdominal cavity. Apex 18 of cone 14 is inserted into defect 43, causing peritoneum 46 to invert inwards into the abdominal cavity. Prosthesis 10 is inserted until mesh sheet 26 is flush with anterior side 48 of fascia 42. Free end 23 of suture 22 is pulled while prosthesis 10 is held in a forward position, i.e. flush with anterior side 48 of fascia 42. The tightening of suture 22 causes opposing cones 14 to be drawn together. The compression of opposing cones 14 causes cones 14 to collapse axially onto themselves, thus causing the diameter of cones 14 to expand radially and pleats 16 to open up or expand into a relatively flattened position. This same action causes tubular structure 28, located within cavity 30, to buckle, collapse and expand outward radially. Knot 24 is pulled until it is fully tightened.

Free end 23 of suture 22 may be provided with a needle to enable attachment of the prosthesis to the surrounding healthy tissue by sewing overlay sheet 26 into place. Alternatively, free end 23 of suture 22 can be trimmed off after final deployment and the overlay patch can be attached in place through the use of additional sutures, or may remain in a flattened condition in the anterior space.

The prosthesis is able to accommodate the spermatic cord structures since it is pleated. When it is expanded, it relies only on the radial expansion force generated from the compression of the opposing textile cones to enlarge the diameter, as opposed to the use of additional semi-rigid rings or other rigid or semi-rigid members. Preferably, prostheses of the present invention do not comprise such rigid or semi-rigid devices. This ensures that the device is fully compliant to the natural anatomical structures.

The final configuration of expanded prosthesis 10, as seen in FIG. 4, both occludes fascia defect 43 on posterior side 47 and is expanded to fill the inner diameter of defect 43 in wall 44. The expansion of radially expandable member 12 on posterior side 47 of defect 43 prevents peritoneum 46 from entering defect 43. Additionally, this posterior expansion ensures that the repair is secure from re-herniation through the defect, since the conical mesh is forced into a relatively flat condition. As the scar tissue grows into the flattened conical layers, it is compressed further in the axial direction by scar tissue contraction. With the inclusion of overlay patch 26, located on anterior side 48 of defect 43, it is virtually impossible for the device to migrate either anteriorly or posteriorly.

In other embodiments of the present invention as illustrated in FIGS. 5–9, the prosthesis is fabricated by cutting a biocompatible, medical textile, preferably polypropylene mesh, into a flat sheet. The sheet is provided with multiple slits, or continuous openings, extending across the width of the flat sheet for a distance effective to provide radial expansion of the radially-expandable member upon deployment of the prosethesis in a fascia defect and, thus, occlusion of the fascia defect. The slits do not extend to the edges of the sheet. The sheet also comprises as an integral part for fixedly attaching the prosthesis to tissue.

Figure 5:
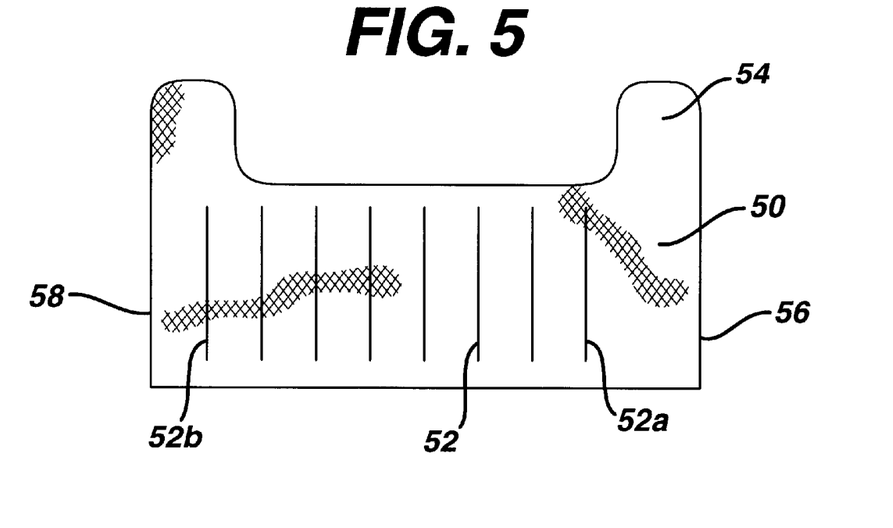
FIG. 5 is a top plan view of a sheet of mesh material used to construct the radially-expandable member depicted in FIG. 7.

As seen in FIG. 5, sheet 50 of mesh is provided with a plurality of slits 52 extending substantially, but not completely, across the width of sheet 50. The number, dimension and location of such slits will be effective to provide radial expansion of the radially-expandable member upon deployment within a defect. It is noted that the distance between slit 52a and edge 56 of sheet 50 is greater than the distance between slit 52b and edge 58 of sheet 50.

While not required or essential to the invention, in certain embodiments, the distance between slit 52a and edge 56 is such that when the sheet is rolled onto itself to form a cylindrical roll, the inner-most layer of sheet material in the rolled cylinder is void of slits. In other words, the distance between slit 52a and edge 56 is equal to or greater than the inner circumference of the rolled cylinder. Sheet 50 also includes tabs 54, for use in subsequent fixed attachment of the prosthesis to tissue.

Figure 6A:
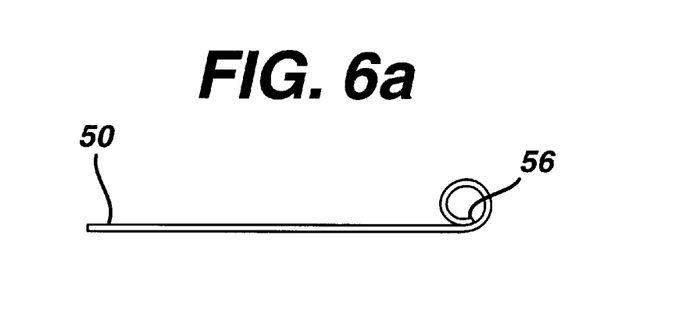
FIG. 6a is an end view of the mesh sheet depicted in FIG. 5 being rolled to form a radially-expandable member.
Figure 6B:
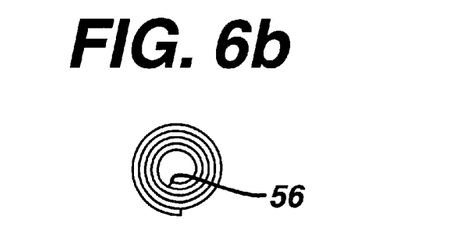
FIG. 6b is an end view of the mesh sheet depicted in FIG. 5 after being rolled to form a radially-expandable member.
Figure 7A:
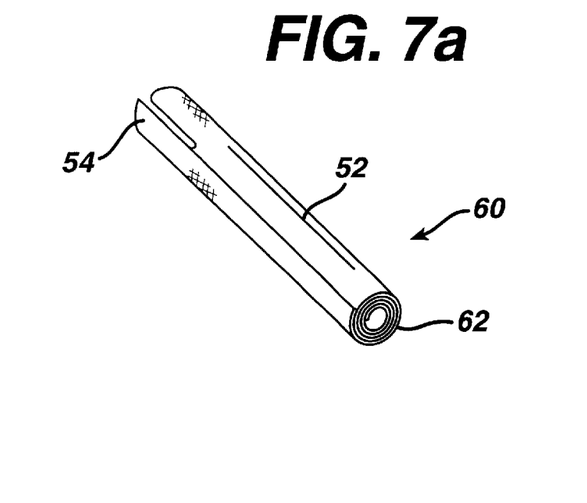
FIG. 7a is a perspective view of a radially-expandable member prepared from the mesh sheet depicted in FIG. 5.
Figure 7B:
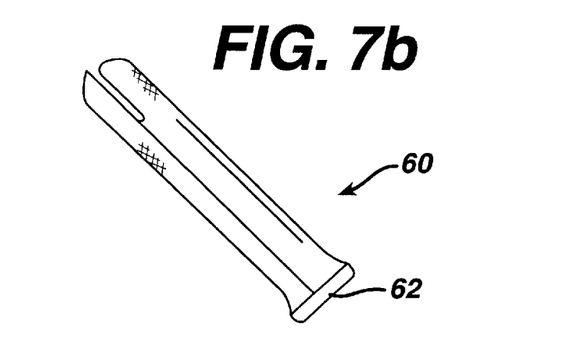
FIG. 7b is a perspective view of a radially-expandable member prepared from the mesh sheet depicted in FIG. 5.

As depicted in FIG. 6a and 6b, sheet 50 is rolled such that edge 56 is rolled into the inner diameter of the cylindrical configuration. The roll is maintained in the cylindrical configuration through the use of tacking welds, sutures or other bonding means at each end of the roll, thus forming the radially-expanding member 60 for occluding a fascia defect, illustrated in FIGS. 7a and 7b. End 62 of radially-expandable member 60 may be sealed closed by stitching, welding or bonding, for example.

Figure 8:
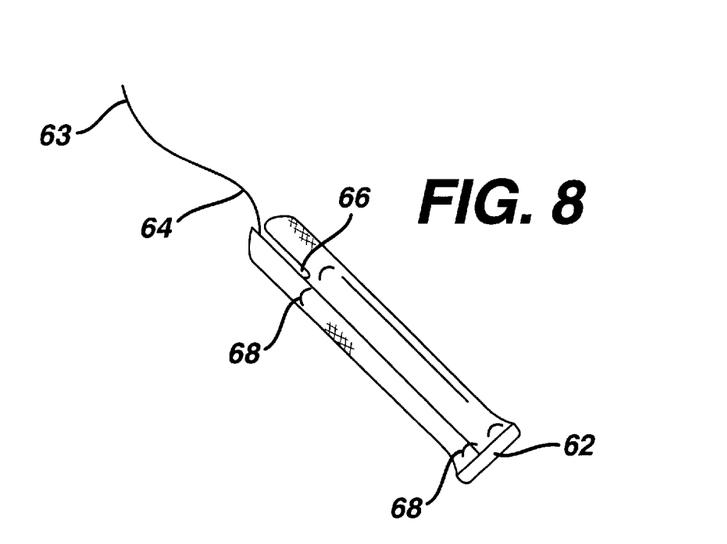
FIG. 8 is a perspective view of a prosthesis according to the present invention.

As seen in FIG. 8, suture 64 is attached to end 62 of radially-expandable member 60 in purse-string arrangement 68, and then tightened and permanently knotted. Free end 63 of suture 64 is passed through the inner part of the rolled cylinder and is stitched around the circumference of open end 66 to form another purse-string arrangement 68. A non-reverse slipknot is tied into the suture.

Figure 9:
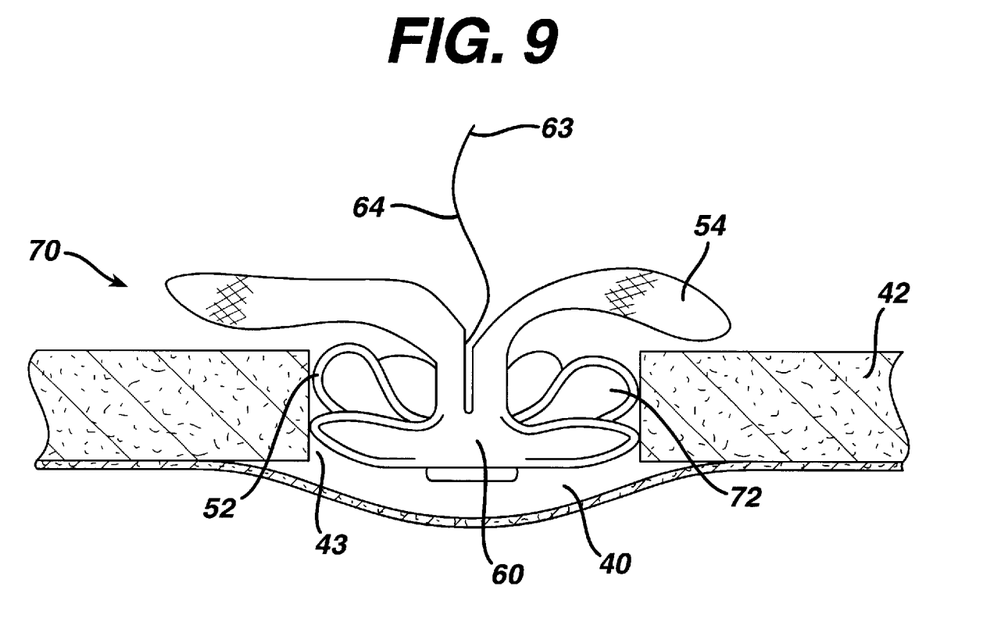
FIG. 9 is a prospective view of the prosthesis depicted in FIG. 8 after deployment, i.e. radial expansion, within the defect.
Figure 10:
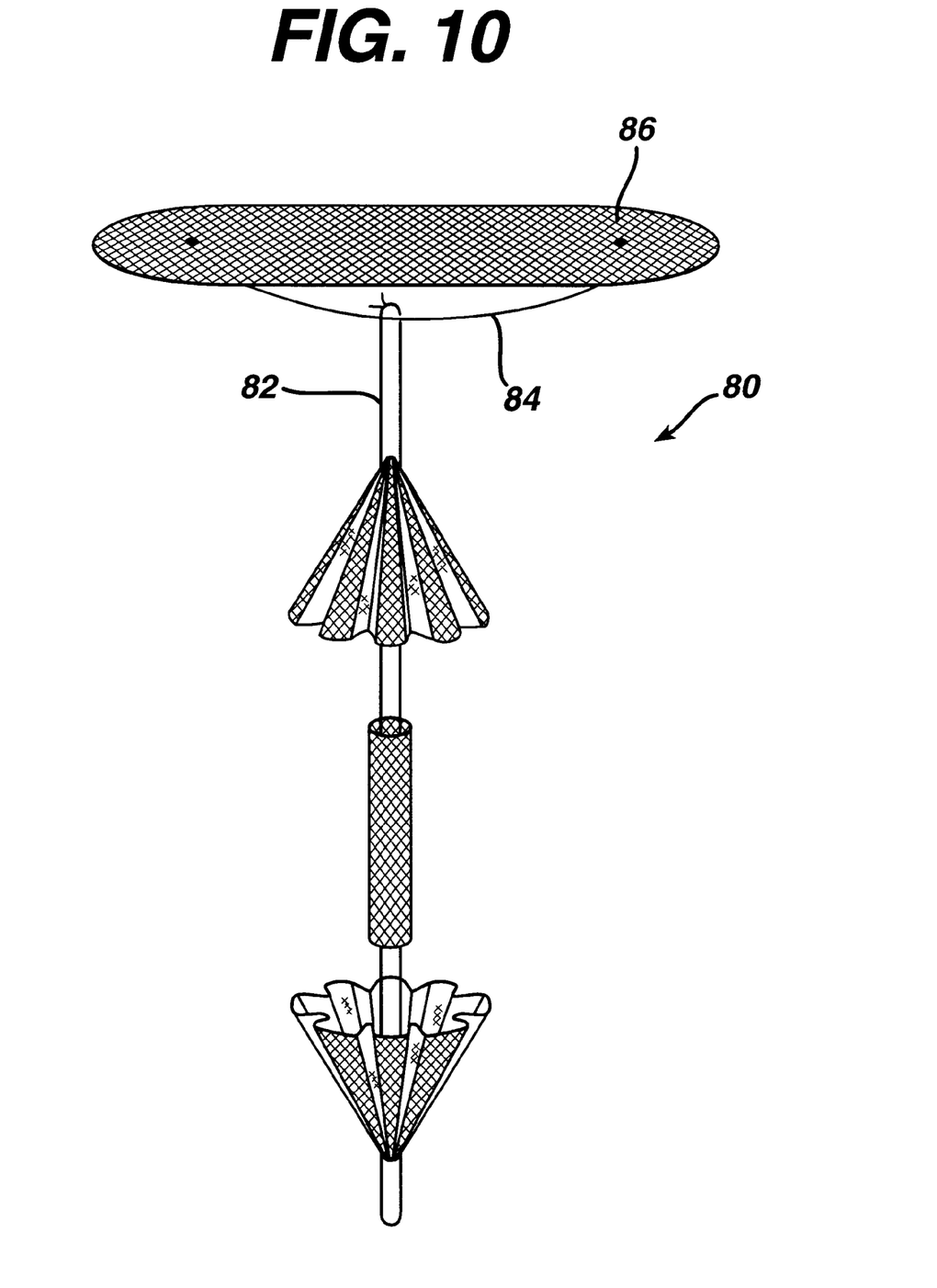
FIG. 10 is a perspective view of a prosthesis according to the present invention.
Figure 11:
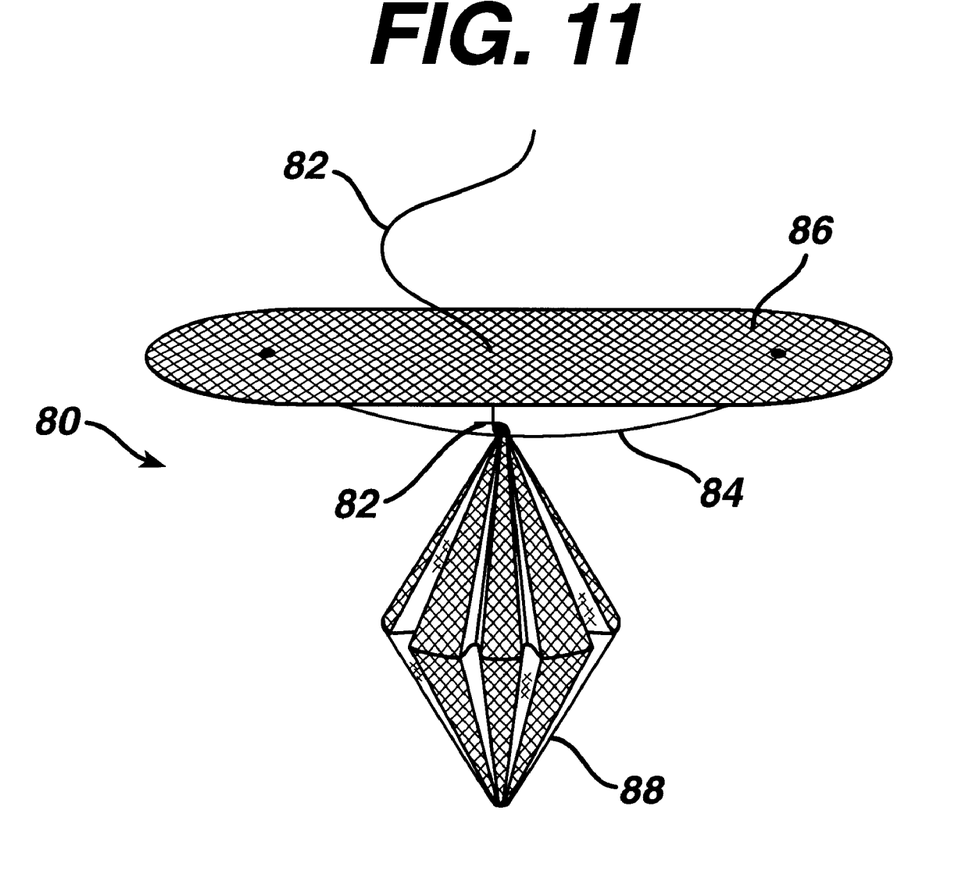
FIG. 11 is a perspective view of the assembled prosthesis depicted in FIG. 10.
Figure 12:
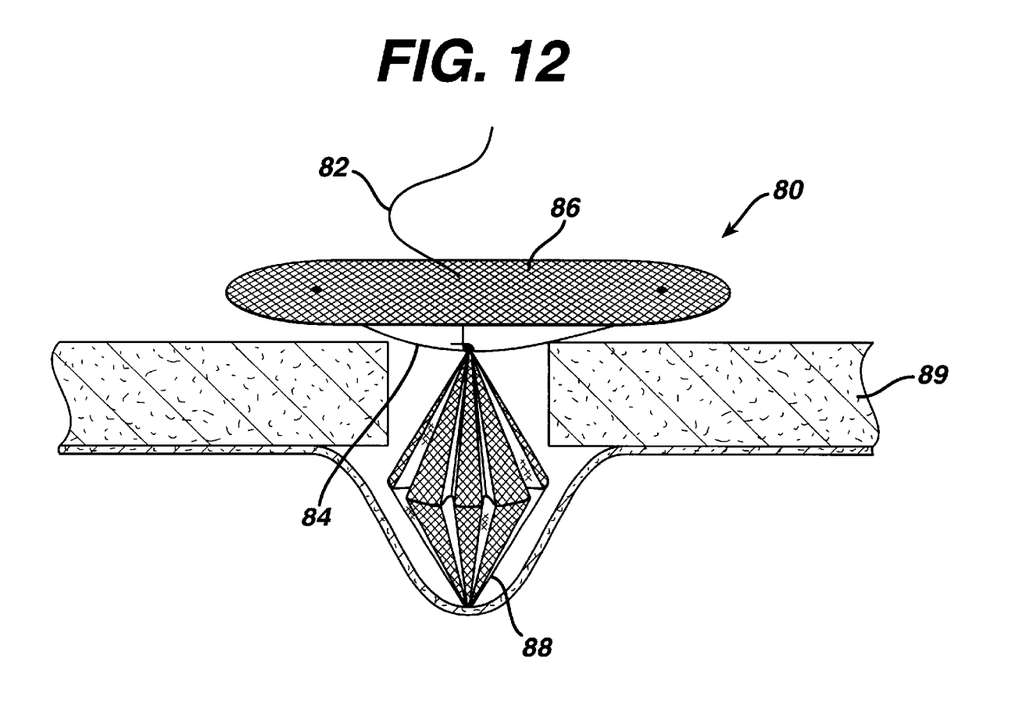
FIG. 12 is a perspective view of the prosthesis depicted in FIG. 11 when positioned within a defect in the fascia.

As depicted in FIG. 9, prosthesis 70 is placed into fascia defect 43 by pressing dissected/ligated hernia sac 40 into the abdominal cavity. Free end 63 of suture 64 is pulled while holding prosthesis 70 forward. As suture 64 is drawn, vertical slits 52 allow radially-expandable member 60 to collapse. Slits 52 buckle outwards, i.e. expand radially, forming overlapping leaves 72 that occlude defect 43. Tabs 54, located at the top of collapsed prosthesis 70, are used to fixedly attach the deployed prosthesis to surrounding healthy tissue.

Figure 13:
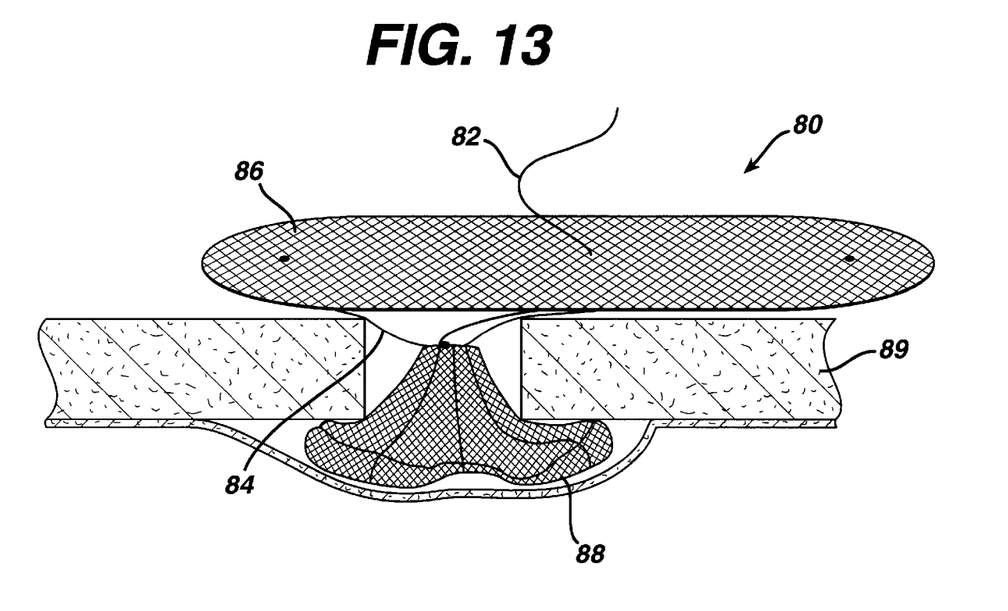
FIG. 13 is a perspective view of the prosthesis depicted in FIG. 12 after deployment, i.e. radial expansion, within the defect.

Referring to FIGS. 10–13, prosthesis 80 comprises overlay patch 86 slideably attached to radially-expandable member 88. As shown, filament 84 is passed through looped suture 82 and affixed at its terminal ends to overlay patch 86. When radial-expandable member 88 is placed in the defect, overlay patch 86 may be maneuvered to one side, as shown in FIG. 13, to effect attachment to fascia 89.

I claim:

1. A hernia repair prosthesis, comprising: a radially-expandable member for placement within and occlusion of a fascia defect, said member comprising a biocompatible, flexible, porous textile suitable for reinforcing fascia defects, wherein said radially-expandable member comprises opposing first and second conical structures, each structure comprising a base and an apex, wherein said structures are fixedly attached one to the other at the respective bases thereof, thereby forming a cavity within said fixedly attached conical structures.

2. The prosthesis of claim 1 wherein said first and second conical structures comprise a plurality of longitudinal pleats terminating at the apex and base of said conical structures.

3. The prosthesis of claim 2 wherein said textile comprises a knitted polypropylene monofilament mesh.

4. The prosthesis of claim 2 wherein said textile comprises a knitted polypropylene monofilament mesh, said prosthesis further comprising a tubular structure of said textile disposed within said cavity.

5. The prosthesis of claim 2 wherein said textile comprises a bioabsorbable mesh.

6. The prosthesis of claim 1 further comprising means for radially-expanding said radially-expandable member.

7. The prosthesis of claim 6 further comprising means for securing said prosthesis to tissue.

8. The prosthesis of claim 4 further comprising means for radially-expanding said radially-expandable member.

9. The prosthesis of claim 8 further comprising means for securing said prosthesis to tissue.

10. The prosthesis of claim 1 wherein said radially-expandable member is slideably attached to a means for securing said prosthesis to tissue.

11. A hernia repair prosthesis, comprising: a radially-expandable member for placement within and occlusion of a fascia defect, said member comprising a biocompatible, flexible, porous textile suitable for reinforcing fascia defects, wherein said radially-expandable member comprises a rolled cylinder of said textile, said cylinder comprising a plurality of longitudinal slits extending substantially along the length of said cylinder.

12. The hernia repair prosthesis of claim 11 further comprising means for radially-expanding said radially-expandable member.

13. The prosthesis of claim 11 further comprising means for securing said prosthesis to tissue.

14. The prosthesis of claim 11 wherein said radially-expandable member is slideably attached to a means for securing said prosthesis to tissue.

* * * * *